United States Patent
Kim et al.

(10) Patent No.: US 10,294,177 B2
(45) Date of Patent: May 21, 2019

(54) METHOD FOR PREPARING ETHYLENE WITH IMPROVED ENERGY EFFICIENCY

(71) Applicant: LG CHEM, LTD., Seoul (KR)

(72) Inventors: Sung-Kyun Kim, Daejeon (KR); Sung-Kyu Lee, Daejeon (KR); Tae-Woo Kim, Daejeon (KR); Joon-Ho Shin, Daejeon (KR); Yeon-Uk Choo, Daejeon (KR); Sa-Eun Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/762,426

(22) PCT Filed: Apr. 7, 2017

(86) PCT No.: PCT/KR2017/003794
§ 371 (c)(1),
(2) Date: Mar. 22, 2018

(87) PCT Pub. No.: WO2017/195989
PCT Pub. Date: Nov. 16, 2017

(65) Prior Publication Data
US 2018/0297915 A1 Oct. 18, 2018

(30) Foreign Application Priority Data
May 10, 2016 (KR) .................. 10-2016-0056943

(51) Int. Cl.
*C07C 7/04* (2006.01)
*C07C 9/06* (2006.01)
*C07C 11/04* (2006.01)
*C07C 11/24* (2006.01)
*C07C 5/09* (2006.01)

(52) U.S. Cl.
CPC .............. *C07C 7/04* (2013.01); *C07C 5/09* (2013.01); *C07C 9/06* (2013.01); *C07C 11/04* (2013.01); *C07C 11/24* (2013.01); *Y02P 20/124* (2015.11)

(58) Field of Classification Search
CPC .......... C07C 7/04; C07C 7/005; C07C 11/04; C07C 11/06; C07C 11/02; C07C 11/24; C07C 9/08; B41J 29/38; B41J 29/393; B41J 25/001; B41J 2/515
See application file for complete search history.

(56) References Cited

U.S. PATENT DOCUMENTS

| | | | |
|---|---|---|---|
| 4,368,061 A | 1/1983 | Mestrallet et al. | |
| 5,220,097 A | 6/1993 | Lam et al. | |
| 5,326,929 A | 7/1994 | Mehra et al. | |
| 7,207,192 B2 * | 4/2007 | Ronczy ................ | F25J 3/0219 62/630 |
| 9,103,586 B2 * | 8/2015 | Verma .................... | C07C 7/005 |
| 2006/0004242 A1 | 1/2006 | Verma et al. | |
| 2006/0021379 A1 | 2/2006 | Ronczy | |

(Continued)

FOREIGN PATENT DOCUMENTS

| KR | 10-0230672 B1 | 11/1999 |
|---|---|---|
| KR | 10-2008-0056104 A | 6/2008 |
| KR | 10-1276943 B1 | 6/2013 |

*Primary Examiner* — Sharon Pregler
(74) *Attorney, Agent, or Firm* — Dentons US LLP

(57) ABSTRACT

Provided is a method for preparing ethylene with improved energy efficiency which can reduce energy due to direct heat exchange between processes.

6 Claims, 2 Drawing Sheets

(56) References Cited

U.S. PATENT DOCUMENTS

2007/0260103 A1 11/2007 Verma et al.
2008/0141713 A1 6/2008 Verma
2009/0326307 A1 12/2009 Panditrao et al.

* cited by examiner

FIG. 1 -- PRIOR ART

METHOD FOR PREPARING ETHYLENE WITH IMPROVED ENERGY EFFICIENCY

TECHNICAL FIELD

This application is a National Stage Entry of International Application No. PCT/KR2017/003794, filed on Apr. 7, 2017, and claims the benefit of and priority to Korean Application No. 10-2016-0056943, filed on May 10, 2016, all of which are hereby incorporated by reference in their entirety for all purposes as if fully set forth herein.

The present invention relates to a method for preparing ethylene with improved energy efficiency, and more preferably, to a method for preparing ethylene with improved energy efficiency, which can reduce energy due to direct thermal exchange between processes.

BACKGROUND ART

Usually, in preparation of ethylene, various methods such as ethane cracking, petroleum degradation, combustion, acetylene hydrogenation and alcohol dehydration have been used. FIG. 1 is a diagram illustrating a conventional process of preparing ethylene, and simply describing the process of preparing ethylene illustrated in FIG. 1, first, when a hydrocarbon compound having two carbon atoms isolated from a De C2 column 2 is transferred to an acetylene converter 4, acetylene ($C_2H_2$) of the hydrocarbon compound having two carbon atoms is converted into ethylene ($C_2H_4$) or ethane ($C_2H_6$). Subsequently, after ethylene and ethane are transferred to a first C2S column 6, a part of the ethylene is isolated first, remaining ethylene and ethane are transferred to a second C2S column 8, followed by isolating and discharging ethylene, and ethane is recycled back to the preceding process, resulting in the obtainment of pure ethylene.

DISCLOSURE OF THE INVENTION

Technical Problem

In the above-mentioned process for preparing ethylene, a refrigerant loop is connected with each column, an energy source such as high-pressure steam is necessary to operate the refrigerant loop. However, in this case, since there is a problem such as a malfunction due to an increased load applied to the refrigerant loop, it is necessary to conduct studies on a method for reducing a load applied to a refrigerant loop by reducing an energy source provided to the refrigerant loop.

Therefore, the present invention is directed to providing a method for preparing ethylene with improved energy efficiency, which can reduce the amount of a refrigerant used and thus reduce energy by installing a heat exchanger between columns used in preparation of ethylene to enable direct heat exchange between the columns.

Technical Solution

To achieve the purpose, the present invention provides a method for preparing ethylene with improved energy efficiency, which includes: providing a C2 compound isolated from a de-ethanizer column to an acetylene converter to convert acetylene of the C2 compound into ethylene and ethane; transferring the C2 compound containing ethylene and ethane converted from acetylene to a first C2 splitter to isolate and discharge a part of the ethylene; and transferring a lower stream containing remaining ethylene and ethane, which are not discharged from the first C2 splitter, to a second C2 splitter, to isolate and discharge the ethylene, and converting the remaining C2 compound containing ethane into ethylene to be recycled. Here, a heat exchanger is installed between the de-ethanizer column and the first C2 splitter to perform direct heat exchange between processes, a difference in pressure between the de-ethanizer column and the first C2 splitter to enable the heat exchange is 4.5 kgf/cm² G or more, and a concentration of ethylene contained in the lower stream of the first C2 splitter is 70 to 80 mol %.

Advantageous Effects

In a method for preparing ethylene with improved energy efficiency according to the present invention, the amount of a refrigerant used can be reduced by installing a heat exchanger between columns used in preparation of ethylene to enable direct heat exchange between columns, resulting in energy savings due to the reduction of energy.

EXPLANATION OF SYMBOLS

10: De-ethanizer column
20: Acetylene converter
30: First C2 splitter
40: Second C2 splitter
50: Heat exchanger

MODE FOR CARRYING OUT THE INVENTION

Hereinafter, the present invention will be described in detail with reference to the accompanying drawings.

Figure 1:
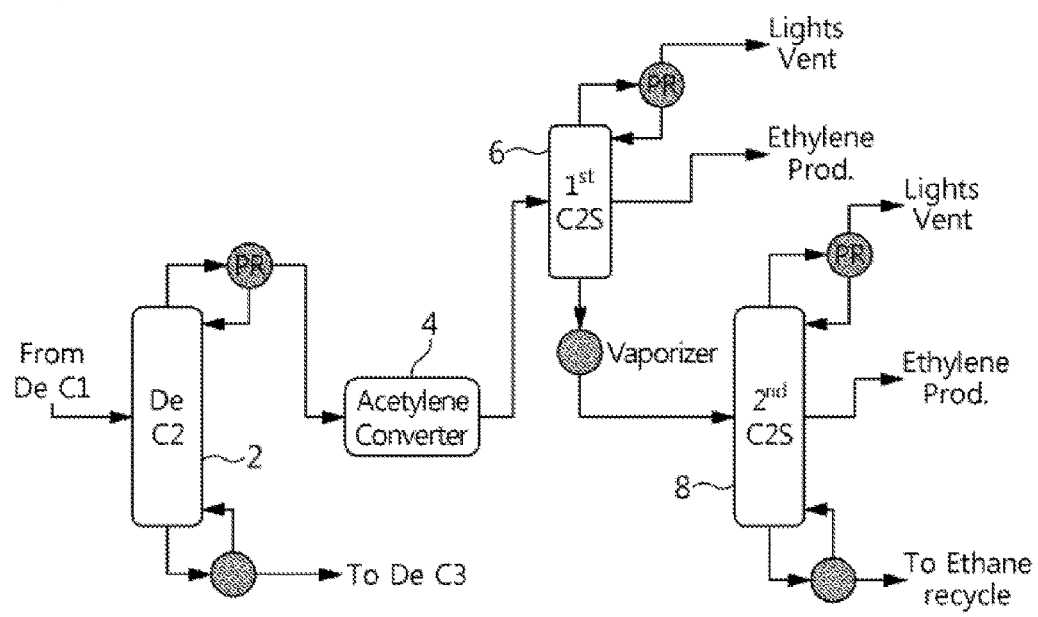
FIG. 1 is a diagram illustrating a conventional process of preparing ethylene.
Figure 2:
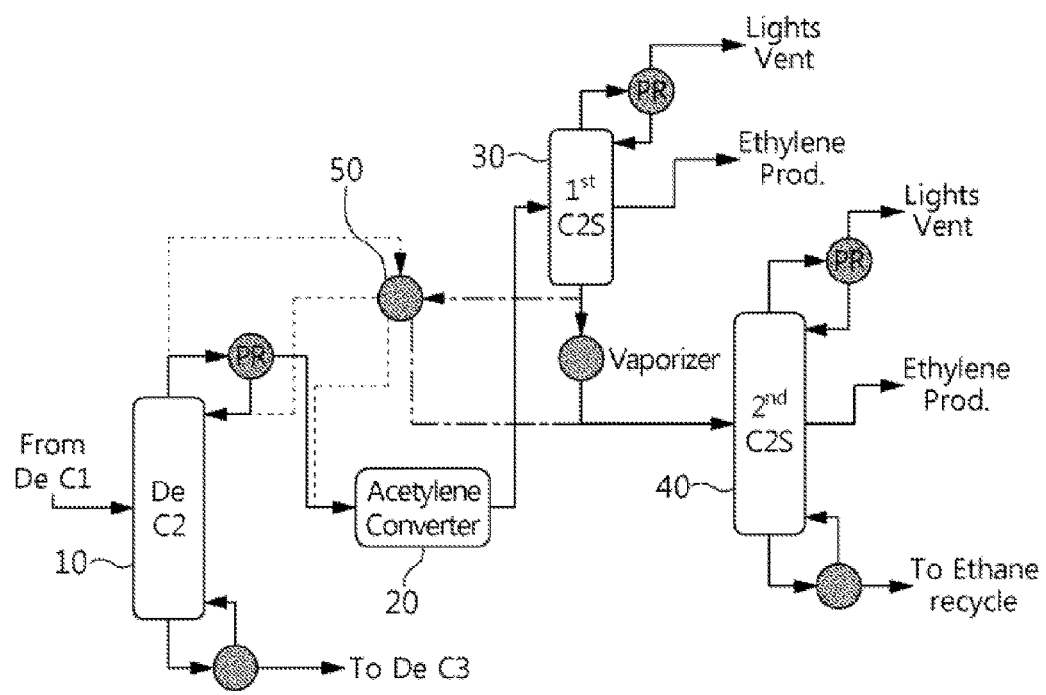
FIG. 2 is a diagram of a process of preparing ethylene for illustrating a method for preparing ethylene with improved energy efficiency according to an exemplary embodiment of the present invention.

FIG. 2 is a diagram of a process of preparing ethylene for illustrating a method for preparing ethylene with improved energy efficiency according to an exemplary embodiment of the present invention. Referring to FIG. 2, the method for preparing ethylene with improved energy efficiency according to the present invention includes: providing a C2 compound isolated from a de-ethanizer column 10 to an acetylene converter 20 to convert acetylene ($C_2H_2$) of the C2 compound into ethylene ($C_2H_4$) and ethane ($C_2H_6$); transferring the C2 compound containing ethylene and ethane converted from acetylene to a first C2 splitter 30 to isolate and discharge a part of the ethylene; and transferring a lower stream containing remaining ethylene and ethane, which are not discharged from the first C2 splitter 30, to a second C2 splitter 40, to isolate and discharge the ethylene, and converting the remaining C2 compound containing ethane into ethylene to be recycled.

A heat exchanger 50 is installed between the de-ethanizer column 10 and the first C2 splitter 30 to perform direct heat exchange between processes, and a difference in pressure between the de-ethane column 10 and the first C2 splitter 30 to enable the heat exchange is 4.5 kgf/cm² G or more, and a concentration of ethylene contained in the lower stream of the first C2 splitter 30 is 70 to 80 mol %.

Describing the method for preparing ethylene with improved energy efficiency in further detail, first, when a hydrocarbon compound having two or more carbon atoms from a de-methanizer column (not shown) is provided to the de-ethanizer column 10, the hydrocarbon compound having two carbon atoms is isolated and transferred to a subsequent stage via the upper part of the de-ethanizer column 10, and a hydrocarbon compound having three or more carbon atoms is transferred to a de-propanizer column (not shown) via the lower part of the de-ethanizer column 10. Subsequently, the hydrocarbon compound having two carbon atoms isolated from the upper part of the de-ethanizer column 10 is transferred and provided to the acetylene converter 20, and acetylene of the hydrocarbon compound having two carbon atoms is converted into ethylene and ethane. Subsequently, the hydrocarbon compound having two carbon atoms containing the ethylene and the ethane converted from the acetylene is transferred to the first C2 splitter 30 and then a part of the ethylene is isolated and discharged. The lower stream of the first C2 splitter 30 containing remaining ethylene and ethane is transferred to the second C2 splitter 40 or provided to the heat exchanger 50, and after being transferred to the second C2 splitter 40, the ethylene is isolated and discharged, and the remaining hydrocarbon compound having two carbon atoms, which contains ethane, is recycled back to the preceding process (particularly, the ethane of the hydrocarbon compound having two carbon atoms is generally returned to an ethane cracker (not shown), and converted into ethylene, where the ethane cracker is a reactor in which a reaction of converting a byproduct produced in the second C2 splitter 40, that is, ethane into ethylene, and is generally included in an NCC process), and therefore, as the above-described process is performed, pure ethylene may be obtained. In addition, light impurities are discharged at the upper parts of the first C2 splitter 30 and the second C2 splitter 40, condensation caused by a refrigerant before discharging may be performed.

Meanwhile, the hydrocarbon compound discharged at the upper part of each of the de-ethanizer column 10, the first C2 splitter 30 and the second C2 splitter 40 is discharged in a vapor form, and condensed by a propylene refrigerant (or a propylene refrigerator; PR). Each condensate obtained by condensation as described above is transferred to a subsequent stage or discharged to the outside, and some of the condensate is used as a heat source for each of the de-ethanizer column 10, the first C2 splitter 30 and the second C2 splitter 40. In addition, the propylene refrigerant (PR) is condensed and cooled in a PR loop, a PR compressor used in the compression of the refrigerant is operated by very high-pressure steam (XS), and after operating the PR compressor, a part of the PR produces high-pressure steam (HS), and the rest thereof is converted into a condensate.

Meanwhile, the C2 compound transferred to acetylene converter 20 after being discharged at the upper part of the de-ethanizer column 10 is most of the hydrocarbon compound having two carbon atoms, and more particularly, refers to a hydrocarbon compound having two carbon atoms and a boiling point (bp) similar to ethylene.

As described in FIG. 2, the present invention can achieve direct heat exchange between processes (or columns), that is, between the de-ethanizer column 10 and the first C2 splitter 30, due to the heat exchanger 50 between the de-ethanizer column 10 and the first C2 splitter 30. Here, the direct heat exchange between the de-ethanizer column 10 and the first C2 splitter 30 is performed between the lower stream of the first C2 splitter 30 and the upper vapor (or upper stream) of the de-ethanizer column 10, and particularly, after the lower stream of the first C2 splitter 30 is provided to the heat exchanger 50, a part of the upper vapor of the de-ethanizer column 10 is condensed (the rest of the vapor is condensed by a refrigerant). That is, this is different from a conventional case in which the lower stream of the first C2 splitter 30 is evaporated by heat provided from a vaporizer, and the upper vapor of the de-ethanizer column 10 is condensed only through heat recovery by a refrigerant.

That is, as described above, when the direct heat exchange between the de-ethanizer column 10 and first C2 splitter 30 is performed, the amount of the propylene refrigerant used in the upper part of the de-ethanizer column 10 is reduced, leading to a reduction in the shaft work of the PR compressor compressing the refrigerant, and very high-pressure steam (XS) required for operation of the PR compressor may be reduced or the output of the high-pressure steam (HS) may be increased by reducing an amount of the condensate.

Meanwhile, an heat exchange amount by the heat exchanger 50 varies according to two operation conditions, that is, a difference (P1–P2) between a pressure (P1) of the de-ethanizer column 10 and a pressure (P2) of the first C2 splitter 30 and a concentration (mol %) of the ethylene contained in the lower stream of the first C2 splitter 30, and direct heat exchange between processes becomes possible when such operation conditions are optimized.

The difference (P1–P2) between a pressure (P1) of the de-ethanizer column 10 and a pressure (P2) of the first C2 splitter 30 is 4.5 kgf/cm$^2$ G or more, and preferably 4.5 to 15 kgf/cm$^2$ G, and when the difference in pressure between the de-ethanizer column 10 and the first C2 splitter 30 is less than 4.5 kgf/cm$^2$ G, it is impossible to ensure the minimum log mean temperature difference (LMTD) required for heat exchange, and thus the heat exchange itself may become impossible.

In addition, the concentration of ethylene contained in the lower stream of the first C2 splitter is 70 to 80 mol %, and when the concentration of ethylene contained in the lower stream of the first C2 splitter 30 is less than 70 mol %, due to a decreased temperature of the ethylene input into the heat exchanger 50, the heat exchange becomes difficult, and when the concentration of ethylene contained in the lower stream of the first C2 splitter 30 is more than 80 mol %, the output of the ethylene of the first C2 splitter 30 is reduced, and thus the process of preparing ethylene becomes inefficient.

Hereinafter, exemplary examples will be provided to help in understanding of the present invention. However, it is apparent to those of ordinary skill in the art that the above descriptions of the present invention are exemplary, and the exemplary embodiments disclosed herein can be easily modified into other specific forms without changing the technical spirit or essential features of the present invention, and such variations and modifications should be within the scope of the appended claims.

EXAMPLES

Example 1

Preparation of Ethylene with Improved Energy Efficiency

In addition to the conventional de-ethanizer column, acetylene converter, first C2 splitter and second C2 splitter for preparing ethylene, a heat exchanger for direct heat exchange between processes was further installed between the de-ethanizer column and the first C2 splitter, and for optimal heat exchange, ethylene was prepared with the difference (P1−P2) between the pressure (P1) of a de-ethanizer column and the pressure (p2) of a first C2 splitter of 4.5 kgf/cm² G, and a concentration of the ethylene in a lower stream of the first C2 splitter of 70 mol %. In the preparation of ethylene, an amount of the final heat exchange, the shaft work of a PR loop used for condensing and cooling a refrigerant and a reduction amount thereof, an amount of very high-pressure steam (XS) used for operating a PR compressor used for compressing a refrigerant, an amount of high-pressure steam (HS) produced after operating the PR compressor, and an amount of high-pressure steam (HS) converted at the same time as a reduction in the amount of condensate obtained by the operation of the PR compressor are shown in Table 1.

TABLE 1

|  | Example 1 | Example 2 | Comparative Example 1 | Comparative Example 2 |
|---|---|---|---|---|
| P1 (kgf/cm² G) | 27.3 | 27.3 | 27.3 | 27.3 |
| P2 (kgf/cm² G) | 22.8 | 22.7 | 22.3 | 23.3 |
| P1 − P2 (kgf/cm² G) | 4.5 | 4.6 | 5.0 | 4.0 |
| Concentration of ethylene in lower stream of first C2 splitter (mol %) | 70.00 | 78.80 | 60.00 | 60.00 |
| Heat exchange amount (Q_HX, Gcal/hr) | 0.035 | 3.0 | 0 | 0 |
| Shaft work of PR loop (kW) | 28314.6 | 27436.0 | 28325.0 | 28325.0 |
| Shaft work reduction amount of PR loop (kW) | 10.4 | 889.0 | 0 | 0 |
| XS input (ton/hr) | 343.87 | 343.87 | 343.87 | 343.87 |
| HS output (ton/hr) | 289.43 | 293.58 | 289.38 | 289.38 |
| HS additional output (ton/hr) | 0.05 | 4.20 | 0 | 0 |

Example 2

Preparation of Ethylene with Improved Energy Efficiency

Ethylene was prepared in the same manner as described in Example 1, except that the difference (P1−P2) between the pressure (P1) of the de-ethanizer column and the pressure (P2) of the first C2 splitter was 4.6 kgf/cm² G, and the concentration of the ethylene in the lower stream of the first C2 splitter was 78.80 mol %. In the preparation of ethylene, an amount of the final heat exchange, the shaft work of a PR loop used for condensing and cooling a refrigerant and a reduction amount thereof, an amount of very high-pressure steam (XS) used for operating a PR compressor used for compressing a refrigerant, an amount of high-pressure steam (HS) produced after operating the PR compressor, and an amount of high-pressure steam (HS) converted at the same time as a reduction in the amount of condensate obtained by the operation of the PR compressor are shown in Table 1.

Comparative Example 1

Preparation of Ethylene

Ethylene was prepared in the same manner as described in Example 1, except that the difference (P1−P2) between the pressure (P1) of the de-ethanizer column and the pressure (P2) of the first C2 splitter was 5.0 kgf/cm² G, and the concentration of the ethylene in the lower stream of the first C2 splitter was 60.00 mol %. In the preparation of ethylene, an amount of the final heat exchange, the shaft work of a PR loop used for condensing and cooling a refrigerant and a reduction amount thereof, an amount of very high-pressure steam (XS) used for operating a PR compressor used for compressing a refrigerant, an amount of high-pressure steam (HS) produced after operating the PR compressor, and an amount of high-pressure steam (HS) converted at the same time as a reduction in the amount of condensate obtained by the operation of the PR compressor are shown in Table 1.

Comparative Example 2

Preparation of Ethylene

Ethylene was prepared in the same manner as described in Example 1, except that the difference (P1−P2) between the pressure (P1) of the de-ethanizer column and the pressure (P2) of the first C2 splitter was 4.0 kgf/cm² G, and the concentration of the ethylene in the lower stream of the first C2 splitter was 60.00 mol %. In the preparation of ethylene, an amount of the final heat exchange, the shaft work of a PR loop used for condensing and cooling a refrigerant and a reduction amount thereof, an amount of very high-pressure steam (XS) used for operating a PR compressor used for compressing a refrigerant, an amount of high-pressure steam (HS) produced after operating the PR compressor, and an amount of high-pressure steam (HS) converted at the same time as a reduction in the amount of condensate obtained by the operation of the PR compressor are shown in Table 1.

Examples 1 and 2 and Comparative Examples 1 and 2

Evaluation of Energy Efficiency Used in Preparation of Ethylene

As shown in Table 1, in Examples 1 and 2 in which two operation conditions are optimized, in other words, the difference (P1−P2) between the pressure (P1) of the de-ethanizer column and the pressure (P2) of the first C2 splitter was set to 4.5 kgf/cm² G or more, and the concentration of the ethylene in the lower stream of the first C2 splitter was set to 70 to 80 mol %, heat exchange was able to be performed (heat exchange amount: Example 1—0.035 Gcal/hr, Example 2—3.0 Gcal/hr), resulting in the reduction of the use of a refrigerant, which can be confirmed by the facts that the shaft work required for the PR compressor used for condensing and cooling a refrigerant was reduced (shaft work reduction amount of the PR compressor: Example 1—10.4 kW, Example 2—889 kW), and that the high-pressure steam (HS) was additionally produced by converting the condensate into the high-pressure steam (HS) at the same time as an amount of the condensate converted by the driving of the PR compressor used in compression of the refrigerant was decreased (HS additional output: Example 1—0.05 ton/hr, Example 2—4.2 ton/hr).

Meanwhile, in Comparative Example 1 satisfying only one (the difference between the pressure of the de-ethanizer column and the pressure of the first C2 splitter) of the two operation conditions, it was confirmed that, like Comparative Example 2 that did not satisfy neither of the two operation conditions, heat exchange cannot be performed, and therefore, it can be seen that, according to the method for preparing ethylene with improved energy efficiency according to the present invention, both of the difference between the pressure of the de-ethanizer column and the pressure of the first C2 splitter and the concentration of the ethylene in the lower stream of the first C2 splitter should be optimized.

The invention claimed is:

1. A method for preparing ethylene with improved energy efficiency, comprising:
    providing a C2 compound isolated from a de-ethanizer column to an acetylene converter;
    converting acetylene of the C2 compound into ethylene and ethane;
    transferring the C2 compound containing ethylene and ethane converted from acetylene to a first C2 splitter to isolate and discharge a part of the ethylene; and
    transferring a lower stream containing ethane and a remaining part of the ethylene of the C2 compound, which are not discharged from the first C2 splitter, to a second C2 splitter, to isolate and discharge the remaining part of the ethylene of the C2 compound, and converting the ethane of the C2 compound into ethylene to be recycled,
    wherein a heat exchanger is installed between the de-ethanizer column and the first C2 splitter to perform direct heat exchange between the de-ethanizer column and the first C2 splitter, a difference in pressure between the de-ethanizer column and the first C2 splitter to enable the heat exchange is 4.5 kgf/cm$^2$ G or more, and a concentration of ethylene contained in the lower stream of the first C2 splitter is 70 to 80 mol %, and
    wherein the heat exchange is performed between the lower stream of the first C2 splitter and an upper stream of the de-ethanizer column.

2. The method of claim 1, wherein a heat exchange amount obtained by the heat exchanger varies according to a difference (P1−P2) between a pressure of the de-ethanizer column (P1) and a pressure (P2) of the first C2 splitter and a concentration (mol %) of the ethylene contained in the lower stream of the first C2 splitter.

3. The method of claim 1, wherein the difference between the pressure of the de-ethanizer column and the pressure of the first C2 splitter is 4.5 to 15 kgf/cm2 G.

4. The method of claim 1, wherein the lower stream of the first C2 splitter is transferred to the second C2 splitter or provided to the heat exchanger.

5. The method of claim 1, wherein the lower stream of the first C2 splitter allows a part of the upper vapor of the de-ethanizer column to be condensed after being provided to the heat exchanger.

6. The method of claim 1, wherein, when the heat exchange is performed between the de-ethanizer column and the first C2 splitter, an amount of a refrigerant used in the upper part of the de-ethanizer column is decreased.

* * * * *